(12) United States Patent
Nissl

(10) Patent No.: US 8,652,196 B2
(45) Date of Patent: Feb. 18, 2014

(54) STENT

(75) Inventor: Thomas Nissl, Winsen/Luhe (DE)

(73) Assignee: Merit Medical Systems, Inc., South Jordan, UT (US)

( * ) Notice: Subject to any disclaimer, the term of this patent is extended or adjusted under 35 U.S.C. 154(b) by 882 days.

(21) Appl. No.: 11/521,720

(22) Filed: Sep. 15, 2006

(65) Prior Publication Data

US 2007/0150049 A1    Jun. 28, 2007

Related U.S. Application Data

(63) Continuation of application No. PCT/DE2004/002719, filed on Dec. 11, 2004.

(30) Foreign Application Priority Data

Mar. 16, 2004  (DE) .......................... 10 2004 012 981

(51) Int. Cl.
*A61F 2/82* (2013.01)

(52) U.S. Cl.
USPC ........................................ 623/1.15; 623/1.34

(58) Field of Classification Search
None
See application file for complete search history.

(56) References Cited

U.S. PATENT DOCUMENTS

| | | | |
|---|---|---|---|
| 5,507,771 A | 4/1996 | Gianturco | |
| 5,741,327 A | 4/1998 | Frantzen | |
| 5,861,027 A | 1/1999 | Trapp | |
| 6,183,506 B1 | 2/2001 | Penn et al. | |
| 6,217,608 B1 * | 4/2001 | Penn et al. | 623/1.16 |
| 6,231,598 B1 * | 5/2001 | Berry et al. | 623/1.15 |
| 6,299,635 B1 | 10/2001 | Frantzen | |
| 6,330,884 B1 | 12/2001 | Kim | |
| 6,375,677 B1 | 4/2002 | Penn et al. | |
| 6,451,049 B2 | 9/2002 | Vallana et al. | |
| 6,485,508 B1 * | 11/2002 | McGuinness | 623/1.15 |
| 6,602,281 B1 * | 8/2003 | Klein | 623/1.15 |
| 6,607,554 B2 * | 8/2003 | Dang et al. | 623/1.15 |
| 6,623,518 B2 | 9/2003 | Thompson et al. | |
| 6,758,860 B1 | 7/2004 | Penn et al. | |

(Continued)

FOREIGN PATENT DOCUMENTS

| | | |
|---|---|---|
| CA | 2304578 | 4/1999 |
| CA | 2446358 | 10/2003 |

(Continued)

OTHER PUBLICATIONS

International Search Report of the International Searching Authority, mailed Apr. 25, 2005 for PCT/US2004/002719 (Filed Dec. 11, 2004).

(Continued)

*Primary Examiner* — Thomas J Sweet
*Assistant Examiner* — Rebecca Preston
(74) *Attorney, Agent, or Firm* — Stoel Rives LLP

(57) ABSTRACT

A stent and associated method for implanting a stent within a body conduit are provided. According to one embodiment, the stent includes a plurality of annular segments arranged peripherally along a longitudinal axis to define opposing free ends, wherein each annular segment includes a plurality of interconnected segment struts. The stent also includes a plurality of connector struts each extending along the longitudinal axis between, and connecting, adjacent annular segments, wherein each connector strut includes an axial section and a compensating section. In addition, at least a portion of each of the segment struts, axial sections, and compensating sections is curved.

12 Claims, 1 Drawing Sheet

(56) References Cited

U.S. PATENT DOCUMENTS

| | | |
|---|---|---|
| 6,786,922 B2 | 9/2004 | Schaeffer |
| 6,796,997 B1 | 9/2004 | Penn et al. |
| 6,858,037 B2 | 2/2005 | Penn et al. |
| 6,881,223 B2 | 4/2005 | Penn et al. |
| 6,887,264 B2 * | 5/2005 | Penn et al. ............... 623/1.15 |
| 6,942,690 B1 * | 9/2005 | Pollock et al. ............ 623/1.15 |
| 2002/0058988 A1 * | 5/2002 | Fischell et al. ............. 623/1.15 |
| 2002/0143386 A1 | 10/2002 | Davila et al. |
| 2002/0198593 A1 * | 12/2002 | Gomez et al. .............. 623/1.16 |
| 2003/0055489 A1 * | 3/2003 | Kveen et al. ............... 623/1.15 |
| 2003/0176912 A1 * | 9/2003 | Chuter et al. .............. 623/1.13 |
| 2004/0088040 A1 * | 5/2004 | Mangiardi et al. ......... 623/1.15 |
| 2004/0102837 A1 * | 5/2004 | Boyle et al. ............... 623/1.16 |
| 2004/0153141 A1 | 8/2004 | Penn et al. |
| 2004/0215325 A1 | 10/2004 | Penn et al. |
| 2004/0236404 A1 | 11/2004 | Penn et al. |
| 2005/0004657 A1 | 1/2005 | Burgermeister |
| 2005/0125051 A1 * | 6/2005 | Eidenschink et al. ....... 623/1.12 |
| 2007/0276463 A1 | 11/2007 | Nissl et al. |

FOREIGN PATENT DOCUMENTS

| | | |
|---|---|---|
| DE | 203 08 672 U1 | 9/2003 |
| DE | 203 12 113 U1 | 9/2003 |
| DE | 2003 08 672 U1 | 9/2003 |
| DE | 2003 12 113 U1 | 9/2003 |
| FR | 2758253 | 7/1998 |
| WO | WO 02/100298 | 12/2002 |
| WO | WO-02/100298 A1 | 12/2002 |

OTHER PUBLICATIONS

Canadian Office Action dated Oct. 31, 2008 for CA Application No. 2,560,001 in the name of Alveolus, Inc.

International Preliminary Report on Patentability for PCT/DE2004/002719, dated Oct. 12, 2006.

* cited by examiner

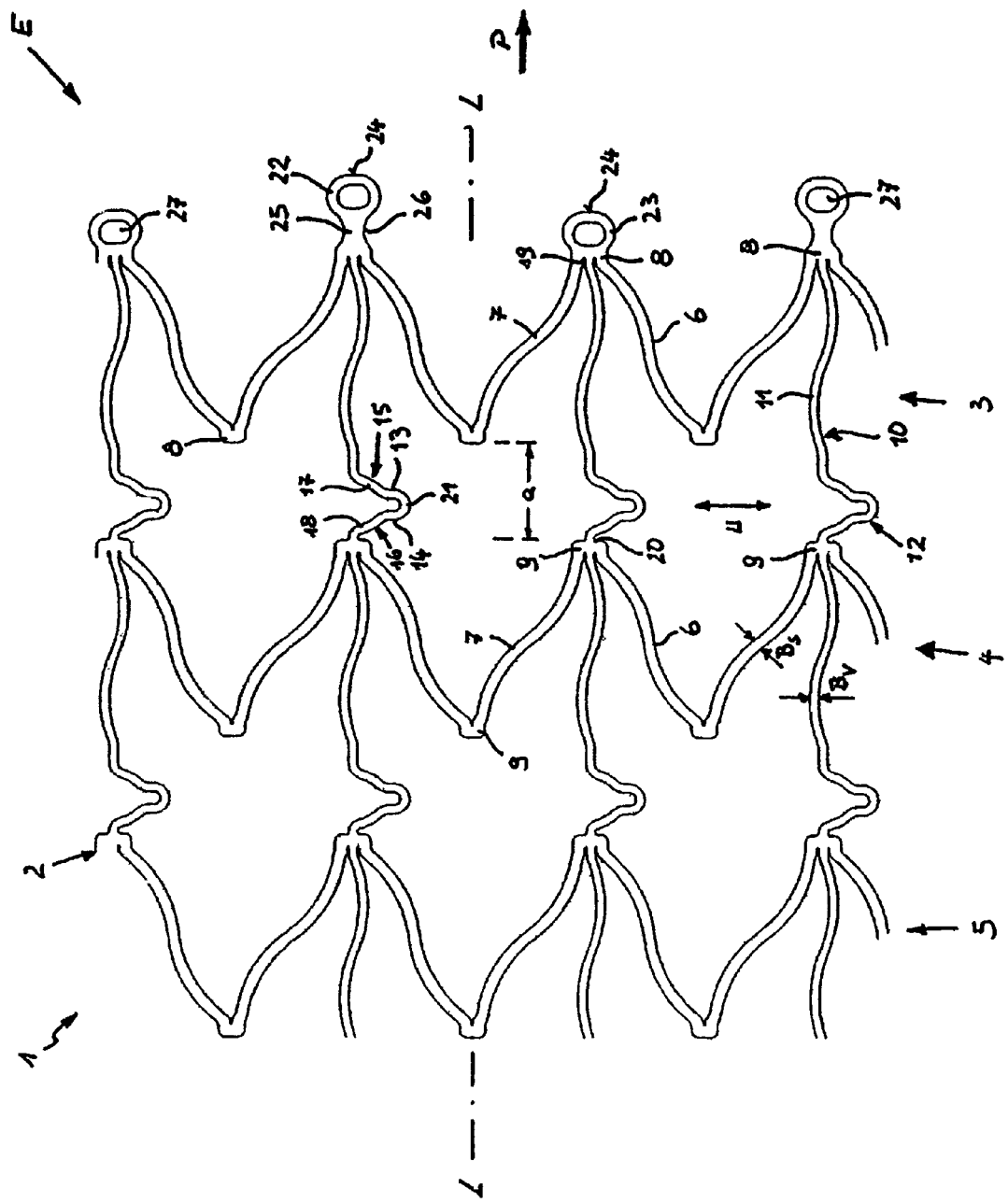

STENT

CROSS REFERENCE TO RELATED APPLICATIONS

The present application is a continuation of PCT Application No. PCT/DE2004/002719 filed Dec. 11, 2004, which claims priority from German Patent Application No. 102004012981.9 filed Mar. 16, 2004, the contents of which are incorporated herein by reference.

BACKGROUND

Stents are used for permanent or also only temporary splinting of body conduits that have become occluded or constricted as a result of stenosis.

The stents have a tubular metal supporting structure consisting of several annular segments. These are formed from segment struts continuously adjoining one another via transition sections. Annular segments adjacent to one another in the longitudinal axis of the stent are coupled by connector struts.

The stents are introduced into the intracorporal vessel by catheter techniques or by using similar insertion aids and are positioned in the area of the stenosis, the supporting structure being able to expand from a contracted insertion state to a supporting state of suitably increased diameter. This expansion can take place automatically in what are called self-expanding stents, but it can also be effected with the aid of a suitable instrument, for example a balloon catheter. In the vessel, the stents function as vascular prostheses for supporting the inside walls of the vessel.

In many applications, for example when used as a biliary stent in the bile ducts, the stent has to be removed again after it has been in the body conduit for a relatively short time, for instance a few months. This is normally done by pulling the stent back into a catheter. The diameter of the expanded stent, sometimes covered with bodily secretions or the like, has to be reduced again. For this, it is desirable that no aspect of the stent geometry gets in the way of pulling it back into a catheter of smaller diameter.

It would therefore be advantageous to provide a stent which, having good compatibility with the vessels in the supporting state, possesses a sufficiently high degree of flexibility and can be easily contracted in order to remove it from a body conduit.

BRIEF DESCRIPTION OF THE SEVERAL VIEWS OF THE DRAWING(S)

FIG. 1 illustrates an enlarged view of an end of a stent in an expanded supporting state according to one embodiment of the present invention.

DETAILED DESCRIPTION OF THE INVENTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

The stent according to one embodiment of the present invention comprises a tubular supporting structure that can be expanded from an insertion state to a supporting state. The supporting structure includes annular segments which follow one another in the longitudinal axis of the stent and which are formed from segment struts continuously adjoining one another in the peripheral direction of the supporting structure. Adjacent annular segments are coupled by connector struts. One aspect of the present invention is that the segment struts are curved in a wave shape, and that each front transition section has an axially protruding widened head end on at least one annular segment located at the end as seen in the longitudinal axis of the stent, head ends that are adjacent in the peripheral direction being arranged offset from one another in the longitudinal axis of the stent and being attached to the adjacent annular segment via connector struts. Furthermore, each connector strut comprises an axial section curved in a wave shape, and also a V-shaped compensating section pointing in the peripheral direction of the supporting structure.

In the stent according to one embodiment of the present invention, at least at one end, each of the transition sections of the segment struts are attached to the nearest adjacent annular segment in each case via a flexible connector strut. In order to remove the stent, the stent can be gripped at this end and pulled into a catheter of smaller diameter. By virtue of the design according to one embodiment of the present invention, the supporting structure can be readily contracted without any outwardly protruding sections of the supporting structure blocking the removal procedure. The stent slides as it were into the catheter in a smooth contracting movement. Even stents covered with adherences or mucous material can be drawn back into the catheter.

The rounded head ends may facilitate a gentle contact of the front ends of the stent on the vessel wall. In the stent according to one embodiment of the present invention, the vessel walls are therefore exposed to less trauma both during insertion and also removal of a stent.

The supporting structure has a wave design, without parallel rectilinear strut sections, and the segment struts can widen from the middle area towards their ends following a continuous profile. This shaping of the segment struts may lead to uniformly distributed tension in the segment struts.

The stent is made of metal. All deformable metals or metal alloys that are medically compatible can be used here, for example stainless steel, cobalt alloys (Phynox), pure iron or, in particular, nickel-titanium alloys (Nitinol).

It may be of interest in practice for the stent according to one embodiment of the present invention to be designed also as a plastic stent. In this connection, the use of bioabsorbable plastics is envisaged in particular. The plastic stent may be configured as an injection-molded part.

The flexibility and contractility of the supporting structure is advantageously promoted if the V-shaped compensating sections in each case have two arms running out in parallel end sections, and the inclined linear sections of the arms have a curved linear course. In this case, each of the compensating sections point with their closed end in the same peripheral direction of the supporting structure. Moreover, the compensating sections are attached directly to the transition sections of an adjacent annular segment.

The width of the connector struts, in particular the width of the axial sections in the connector struts, is typically less than the width of the segment struts of the annular segments.

A measure improving the use of the stent according to one embodiment of the present invention is that the transition sections have an axially protruding widened head end on the annular segment located at the end as seen in the longitudinal axis of the stent, adjacent head sections being arranged offset from one another in the longitudinal axis of the stent. Each second head end is connected to a transition section via a coupling section, the coupling section having concavely rounded side grooves. The side grooves engage partially around the adjacent head ends when the supporting structure is in the insertion state and cover these.

The advantageously rounded head ends may facilitate gentle contact of the ends of the stent on a vessel wall. In this way, the vessel walls may be exposed to less trauma both during the insertion and also during the removal of a stent. In the contracted state, the head ends cover the adjacent transition sections. Thus, the risk of injury to the surrounding vessel walls may be reduced.

The function of the head ends can be further improved if they are designed in the form of eyelets and are provided with a recess. Thus, the head ends can be used for gripping the stent with a suitable instrument or in order to wind or loop a thread through the head ends. The thread ends may be deflected into the interior of the supporting structure and connected to one another by a connector, such as a material that is visible under X-ray. For removing the stent, the thread ends can be gripped at the connector. By pulling the thread, the thread is contracted and the looped annular segment of the supporting structure is drawn together, whereupon the stent can be removed from the body conduit. This configuration aids in the explanation of a stent.

Referring to FIG. 1, a stent 1 according to one embodiment of the present invention is illustrated. The stent 1 is made of metal and comprises a tubular supporting structure 2 including several annular segments 3, 4, 5 following one behind the other. The length of the stent 1 can in principle vary. As has been mentioned, only one end section is shown here, not the full number of annular segments 3, 4, 5 of the stent 1.

The annular segments 3, 4, 5 are formed from segment struts 6, 7 curved in a wave shape and extending obliquely with respect to the longitudinal axis L of the stent 1, said segment struts 6, 7 continuously adjoining one another in a zigzag pattern via transition sections 8, 9. The annular segments 3, 4, 5 are coupled to one another by connector struts 10. It will be noted that each transition section 8 of the annular segment 3 located at the end in the longitudinal axis L of the stent is connected via a connector strut 10 to the transition section 9 of the adjacent annular segment 4. Each connector strut 10 comprises an axial section 11 curved in a wave shape, and also a V-shaped compensating section 12 pointing in the peripheral direction U of the supporting structure. The compensating sections 12 are in each case arranged in the space between the adjacent annular segments 3, 4 and 4, 5 with axial spacing a. The width $B_V$ of the axial sections 11 is thinner than the width $B_S$ of the segment struts 6, 7. The compensating sections 12 each have two arms 15, 16 that run out and converge into parallel end sections 13, 14. The inclined linear sections 17, 18 of the arms 15, 16 have a curved linear course.

The connector struts 10 each extend from the transition section 8 at the deepest point 19 of two closed segment struts 6, 7 of an annular segment 3 or 4 as far as the transition section 9 at the peak 20 of two closed segment struts 6, 7 of the adjacent annular segment 4 or 5, the compensating sections 12 being attached directly to the transition sections 9. The compensating sections 12 all point with their closed ends 21 in the same peripheral direction U.

The front transition sections 8 on the end annular segment 3 each have an axially protruding widened head end 22, 23 with a concavely rounded front section 24. Head ends 22, 23 that are adjacent in the peripheral direction U are arranged offset from one another. For this purpose, the head ends 22 are connected to the transition sections 8 via a coupling section 25, such that the head ends 22 protrude axially in relation to the head ends 23.

The coupling sections 25 have concavely rounded side grooves 26. In the contracted state for insertion of the supporting structure 2, the head ends 22 engage partially around the adjacent head ends 23 and cover them. The head ends 23 are thus protected and concealed by the head ends 22.

In this way, the vessel walls may suffer less trauma both during insertion and also during removal of a stent 1. Moreover, the rounded head ends 22, 23 may ensure that the stent 1 bears gently on the vessel wall when it is being inserted.

It will also be noted that the head ends 22, 23 are designed in the form of eyelets and have recesses 27. The stent 1 can be gripped at the recesses 27 in order to remove it from a body conduit and can be pulled into a catheter in the direction of the arrow P. The proximal end E can also be additionally contracted, for example, with the aid of a thread looped through the recesses 27.

One advantageous aspect for explanation of a stent 1 relates to the configuration of the supporting structure 2 with the wave-shaped segment struts 6, 7 and the configuration of the connector struts 10 with the wave-shaped axial section 11 and the compensating section 12, where the axial sections 12 are thinner than the segment struts 6, 7. This enhances the flexibility and sliding properties of the stent 1. A further aspect of the present invention is that each transition section 8 at the free end E of the stent 1 or of the annular segment 3 are each connected to the adjacent annular segment 4 via a connector strut 10. This has the effect that the stent 1 may be drawn together and pulled in the direction of the arrow P such that the stent may reduce or eliminate the incidence of creating an obstruction during the explanation procedure. The stent 1 can thus be gripped and removed from a body conduit in the direction of the arrow P.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

LIST OF REFERENCE SIGNS 1 stent
2 supporting structure
3 annular segment
4 annular segment
5 annular segment
6 segment strut
7 segment strut
8 transition section
9 transition section
10 connector strut
11 axial section
12 compensating section
13 end section
14 end section
15 arm
16 arm
17 linear section
18 linear section 19 deepest part
20 peak
21 end of 12
22 head end
23 head end
24 front section
25 coupling section
269 side groove
27 clearance
L longitudinal axis of stent
U peripheral direction
a spacing
E end of 1
P arrow
$B_v$ width of 11
$B_S$ width of 6, 7

That which is claimed:

1. A stent comprising:
a plurality of annular segments arranged peripherally along a longitudinal axis to define opposing free ends, each annular segment comprising a plurality of interconnected segment struts; and
a plurality of connector struts each extending along the longitudinal axis between, and connecting, adjacent annular segments, each connector strut comprising an axial section and a compensating section, wherein at least a portion of each of the segment struts, axial sections, and compensating sections is curved, wherein each of the compensating sections comprises a V-shaped section having a pair of curved inclined sections, wherein each of the segment struts and axial sections continuously curve along their respective lengths, wherein a pair of segment struts is configured to conform to each axial section along their respective lengths in a contracted state, and wherein a plurality of adjacent segment struts are adjoined to one another via a transition section, the transition section being directly attached to an adjacent compensating section.

2. The stent according to claim 1, wherein each of the segment struts and axial sections is curved in a wave shape.

3. The stent according to claim 1, wherein each of the segment struts extends obliquely with respect to the longitudinal axis.

4. The stent according to claim 1, wherein each of the compensating sections comprises a pair of arms extending parallel to one another and from the pair of curved inclined sections to define a closed end.

5. The stent according to claim 4, wherein each of the closed ends extend in a same peripheral direction.

6. The stent according to claim 1, further comprising a plurality of head ends extending from respective transition sections at one or more of the free ends.

7. The stent according to claim 1, wherein a width of at least a portion of each of the connector struts is less than a width of each of the segments struts.

8. The stent according to claim 7, wherein a width of each axial section is less than a width of each segment strut.

9. The stent according to claim 1, wherein each of the segment struts widens from a middle area to its respective ends.

10. The stent according to claim 1, wherein each annular segment comprises a plurality of segment struts defining a plurality of peaks and valleys each extending in a same axial direction along the longitudinal axis, and wherein each of the plurality of connector struts extends between respective peaks of the segment struts.

11. A stent comprising:
a plurality of annular segments arranged peripherally along a longitudinal axis to define opposing free ends, each annular segment comprising a plurality of interconnected segment struts; and
a plurality of connector struts each extending along the longitudinal axis between, and connecting, adjacent annular segments, the plurality of the connector struts comprising:
an axial section connected to a given annular segment of the plurality of annular segments; and
a compensating section, comprising:
a pair of arms oppositely curved and inclined, a first arm of the pair of arms connecting to the axial section, and a second arm of the pair of arms connecting to an annular segment of the plurality of annular segments that is adjacent to the given annular segment;
parallel end sections connecting to the pair of arms; and
a closed end connecting the parallel end sections;
wherein each of the interconnected segment struts and connector struts continuously curve along at least a portion of their respective lengths.

12. The stent according to claim 11, wherein at least a portion of each of the segment struts and connector struts is curved in a wave shape.

* * * * *